(12) United States Patent
Heppler

(10) Patent No.: US 8,512,363 B2
(45) Date of Patent: Aug. 20, 2013

(54) CHANNELED WIRE GUIDE FOR A SCALPEL

(76) Inventor: J. Scott Heppler, Yakima, WA (US)

( * ) Notice: Subject to any disclaimer, the term of this patent is extended or adjusted under 35 U.S.C. 154(b) by 143 days.

(21) Appl. No.: 12/932,716

(22) Filed: Mar. 4, 2011

(65) Prior Publication Data
US 2012/0226299 A1 Sep. 6, 2012

(51) Int. Cl.
*A61B 17/32* (2006.01)

(52) U.S. Cl.
USPC ......................................................... 606/167

(58) Field of Classification Search
USPC .................. 606/167, 170, 185; 30/340, 127, 30/123.5, 329–339, 286–295; 83/270, 279, 83/373, 743, 761–764, 780, 438–440, 442, 83/448–450, 454, 455, 635, 638, 821; 604/164.01; 206/352–358; 7/161
See application file for complete search history.

(56) References Cited

U.S. PATENT DOCUMENTS

| 2003/0180678 A1* | 9/2003 | Kesling et al. ................. 433/8 |
| 2004/0181246 A1* | 9/2004 | Heppler ...................... 606/167 |

* cited by examiner

*Primary Examiner* — Ryan Severson
*Assistant Examiner* — Katherine M Shi
(74) *Attorney, Agent, or Firm* — Svendsen Legal, LLC.

(57) ABSTRACT

A scalpel guide system for a bladed surgical instrument. A pair of wire guides attach to a scalpel, for controlled travel of the scalpel along the wire. The wire guides of the scalpel guide system are especially useful as an enhancement to the "Seldinger technique," or any surgical procedure employed for the percutaneous placement of elongated, tubular devices, with the aid of a guidewire or filament wire. The scalpel can be any knifelike surgical device, conventionally including a blade attached to a handle. The scalpel guiding system preferably includes a pair of wire guides, each extending from the scalpel, which can be disposable, as can the blade, independent of the scalpel. The pair of wire guides each have generally open funnel-shapes, with their wider portion facing the gap formed between the two guides. The user places this medal gap on the wire and rotates the scalpel to engage the wire. This engagement allows the user or surgeon to move the scalpel along the wire in a controlled and guided manner, for precise cutting or incising, as required for the needed procedure or operation.

12 Claims, 3 Drawing Sheets

CHANNELED WIRE GUIDE FOR A SCALPEL

TECHNICAL FIELD

The invention relates to a guide system for a bladed surgical instrument, and more particularly to a pair of scalpel attached wire guides, each with a narrowing channel or funnel shape, for controlling travel of the scalpel along an engaged wire.

BACKGROUND OF THE INVENTION

There are many percutaneous medical devices that function to evacuate air or fluid from body cavities. Conventional catheters may be inserted using a guidewire and moved into the body to almost any desired location. Once located in position, the guidewire is typically removed. Other similar functioning percutaneous devices function to administer a substance, such as a drug, into the body cavity or into a vascular lumen. Most of these devices are elongated and tubular, sharing a common method of placement over or with the aid of the guidewire. A common method for placement of these devices employing a guidewire, is known as the "Seldinger technique."

The Seldinger technique has revolutionized the practice of medicine by allowing procedures that were previously done with "open" surgical technique to be performed with "closed," percutaneous technique. As is evident from the following description of the Seldinger technique, the "closed" percutaneous method results in an incision that is just large enough to pass the medical device via a needle initiated "tract" down to the desired, hollow cavity or "lumen."

To perform the Seldinger technique, a hollow hypodermic needle of the necessary length and rigidity to reach the desired body cavity or lumen is passed through the skin surface until the distal tip of the needle is in the cavity or lumen. The needle is often of a much smaller diameter than the medical device that will subsequently be placed in order to minimize damage in the event the cavity or lumen is missed initially. The position of the distal tip of the needle is then verified by aspirating the appropriate body fluid or air into a syringe. In difficult to access cavities or lumens, fluoroscopic or other radiologic imaging can be utilized to guide and confirm placement. A flexible guidewire is then passed into the proximal hub of the needle, through the lumen of the needle and into the cavity or lumen. Control is maintained at the distal aspect, or exposed length of the guidewire. Next, the guidewire is held in position while the needle is withdrawn over the distal aspect of the guidewire and removed entirely from the distal end of the guidewire.

The elongated, tubular medical device, commonly known as a catheter or a drainage tube, can be too large and too pliable to easily pass over the guidewire, through the needle tract made in the skin and tissues, and into the desired body cavity or lumen. Often, a superficial dermatotomy, commonly referred to as a "skin-nick," is then performed with a surgical scalpel blade immediately adjacent to the entry of the guidewire, to enlarge the entry site. A rigid dilator is often then passed over the guidewire to enlarge the deeper aspects of the tract and allow the subsequent medical device to pass smoothly over the guidewire into the desired cavity or lumen.

A well-made skin nick should contain the guidewire and should be large enough to admit the medical device. It should not be so large or so deep as to allow leakage of body fluids around the subsequently placed medical device, or to excessively compromise the function of the skin as a barrier to infection. If the nick is made away from the entry site of the wire or is not sufficiently deep, the dilator, and or the medical device, will not pass over the guidewire and through the skin and tissues easily. If excessive force is employed, the tip of the dilator, and or the medical device, can flare and bind at the skin surface.

In spite of the fact that a guidewire leads to the precise place where the skin nick is to be made, the dermatotomy is often performed with a traditional scalpel, employing only the visual guidance and the free hand of the operator. In urgent settings, with poorly positioned patients, in poorly lighted rooms, a precisely placed skin nick can require significant concentration at a time when there are other pressing issues with the patient.

Devices produced to minimize these safety and procedural difficulties, as encountered in performing dermatotomies in conjunction with percutaneous placements of guidewires or the like, include the type found in U.S. Pat. No. 7,341,596 to J. Scott Heppler, which is useful in minimizing the potential for inadvertent lacerations in the precise performance of skin-nicks, to which the present device further improves. The present invention addresses these needs and will be better understood by reference to the following detailed description taken in conjunction with the accompanying drawings.

DETAILED DESCRIPTION OF SPECIFIC EMBODIMENTS

The present invention provides a guide system for a scalpel, and specifically a system of channeled or funnel-shaped guides for receiving a wire onto a bladed surgical instrument, to guide the movement of the scalpel along the wire, and orient the blade such that the subsequent incision is immediately adjacent to the guidewire entry point. The guides receive the wire, to restrict the travel of the bladed surgical instrument along the wire. The guide system 25 for a scalpel 27 is shown in FIGS. 1 through 4B. The scalpel guide system is especially useful as an enhancement to the "Seldinger technique." As discussed in the foregoing section, the Seldinger technique is a common surgical procedure for the percutaneous placement of elongated, tubular devices, with the aid of a "guidewire," or simply referred to herein as a wire 29. The Seldinger technique may be performed by any qualified user 26 of the scalpel, who is typically a surgeon or other person similarly qualified in the pertinent medical arts. The scalpel is also referred to herein, as a "bladed surgical instrument," and is employed in the Seldinger technique.

Figure 4A:
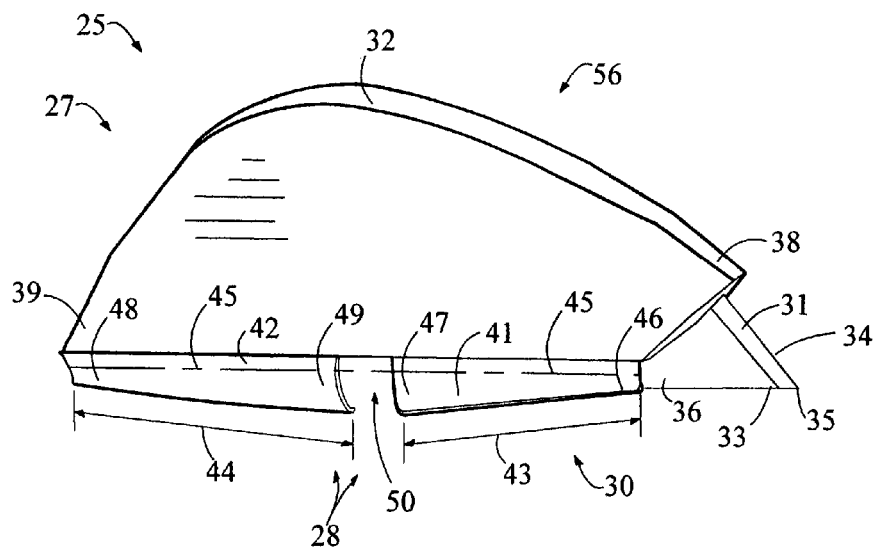
FIG. 4A is a perspective view of a guide system for a scalpel, according to an embodiment of the invention.

The "wire" 29 is broadly defined for the purposes of the present invention, and can be any such guidewire, bundle of wires, filament, bundle of filaments, strands, bundle of strands, or bundles of any various combination of wires, filaments or strands, as conventionally employed in surgical techniques that involve the insertion of such wires, strands, filaments, or bundles. For example, the wire may be a wound wire, a single metal, a plastic or composite strand, a hollow and elongated catheter, a fiber optic cable or bundle, or a braided wire. The wire has a continuous length 36, which is an inherent property for any such wire or filament. Additionally, the wire has a wire centerline 37, which follows a cross sectional center 40 of the wire, as shown in FIG. 4A. Alternatively, any wire with the ability to meet the basic function of being engageable by the pair of wire guides 28, as mounted to the scalpel or equivalent bladed surgical instrument 27, is considered appropriate for use with the present invention.

Figure 1:
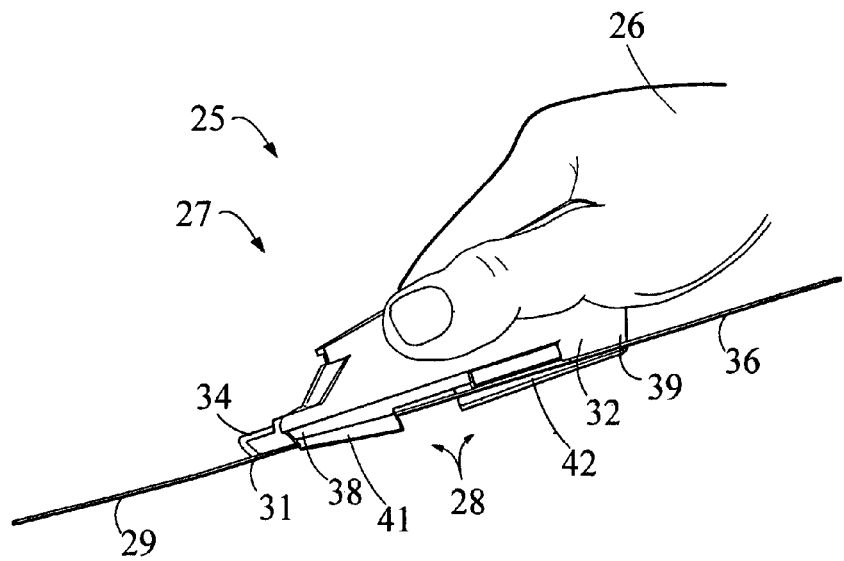
FIG. 1 is a perspective view of a guide system for a scalpel, according to an embodiment of the invention.
Figure 2:
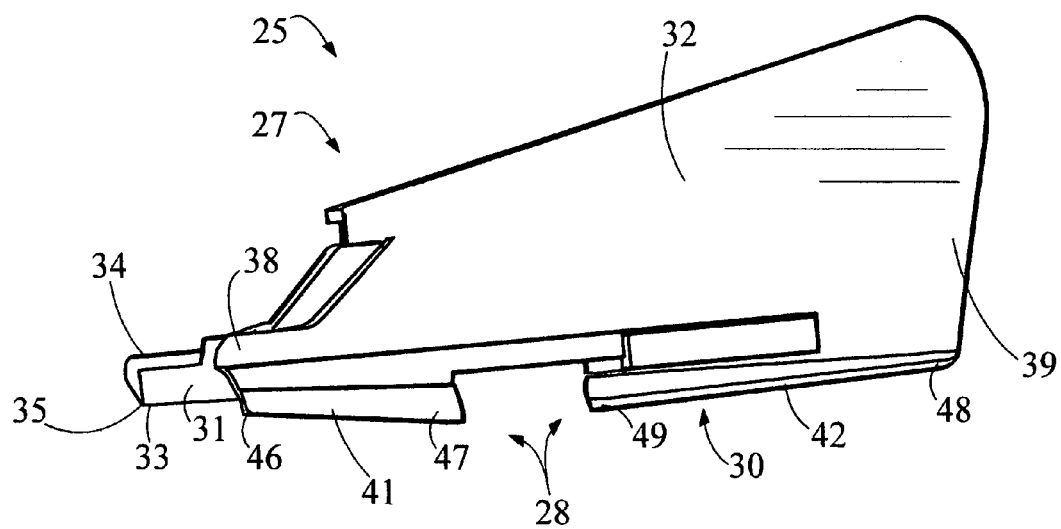
FIG. 2 is a side view of a guide system for a scalpel, according to an embodiment of the invention.
Figure 4B:
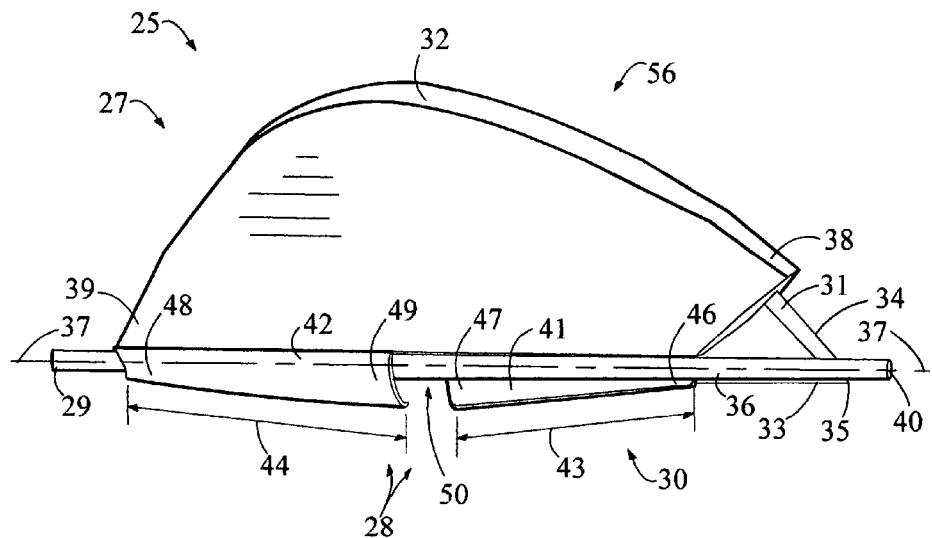
FIG. 4B is a perspective view of a guide system for a scalpel, according to an embodiment of the invention.

As detailed in FIGS. 1 and 2, the scalpel 27 employing the guide system 25 of the present invention preferably includes a pair of wire guides 28, attached to the scalpel, with each of the pair of wire guides having a generally open funnel-shape 30, as detailed in FIGS. 2, 4A, and 4B. Each wire guide extends from the scalpel, and for the present invention, the scalpel can be any knifelike, bladed surgical instrument or device, conventionally including a blade 31 attached to a handle 32. The handle can be formed of a plastic, or of a metal. Plastic handles are typically employed in disposable scalpel designs, and metal handles utilized in reusable, "autoclaveable" instruments. The handle is formed to be conveniently grasped by the user 26, with certain handles including safety features to either extend the blade from the handle or retract a safety shield from the blade, when the scalpel is in use. Typically, the blade includes a lower contacting edge 33, often separated from an upper cutting edge 34 by a point 35, as shown in FIG. 2. Most preferably, the lower contacting edge is a non-cutting edge that contacts the wire 29 and slides smoothly along the wire without catching or cutting into the wire. However, the blade can be any shape, as desired or needed for a particular procedure, including a rounded blade, substantially without the point of the blade, where the lower contacting edge smoothly transitions into the upper cutting edge.

Figure 3A:
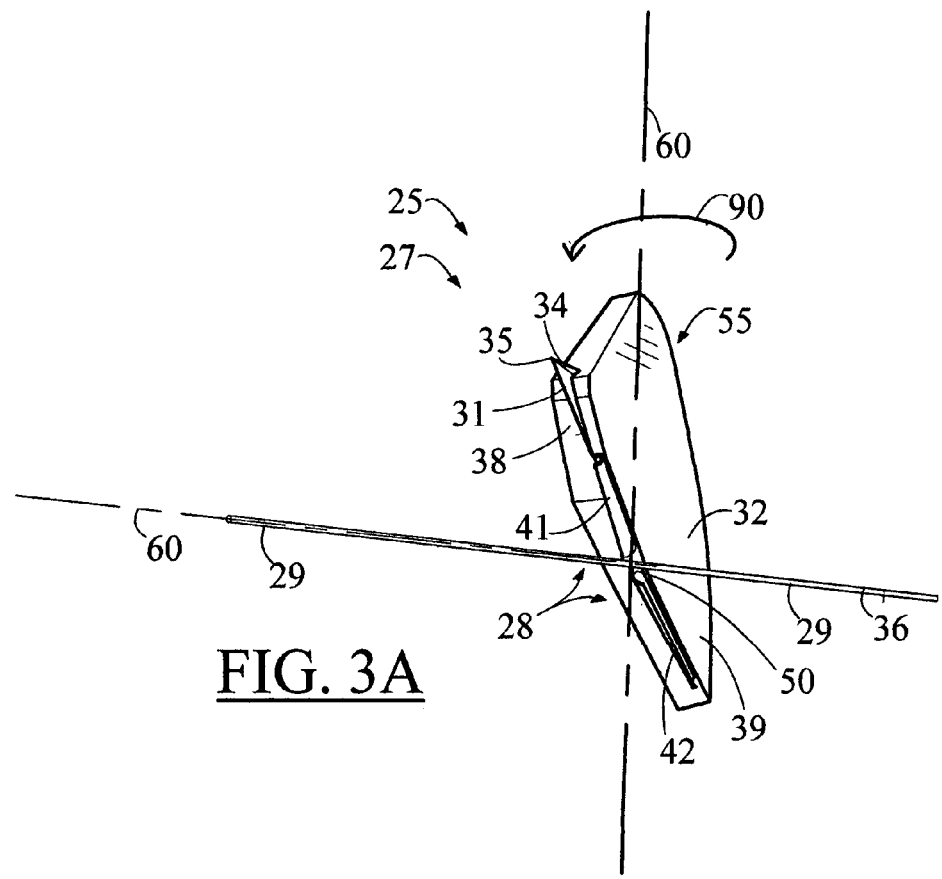
FIG. 3A is a perspective view of a guide system for a scalpel, according to an embodiment of the invention.

As shown in FIG. 3A, the guide system 25 for a bladed surgical instrument includes the pair of wire guides 28, and each extends from the bladed surgical instrument 27 or scalpel, as noted above. The scalpel includes a forward end 38 opposite a rearward end 39. Preferably, the blade 31 of the scalpel is located proximate to the forward end, and the handle 32 extends toward the rearward end, with the scalpel handle for grasping by the user 26.

As detailed in FIG. 2, the pair of wire guides 28 includes a forward guide 41 that is located proximate to the forward end of the bladed surgical instrument 27, and a rearward guide 42 located proximate to a rearward end of the bladed surgical instrument. The forward guide has a forward guide length 43 and the rearward guide has a rearward guide length 44.

As noted above, the pair of wire guides each have a generally open funnel-shape 30. The forward guide 41 includes a narrow fore-channel portion 46 that is located proximate to the forward end 38 of the scalpel 27. This forward end location of the narrow fore-channel portion on the scalpel is preferably close in proximity to the blade 36, of the scalpel. The forward guide also includes a wide back-channel portion 47 that is located toward the rearward end 39 of the scalpel. As shown in FIG. 2, the forward wire guide expands from the narrow fore-channel portion to the wide back-channel portion, along the forward guide length 43.

In a mirror relation to the forward guide 41, the rearward guide 42 includes a narrow back-channel portion 48 that is located proximate to the rearward end 39 of the scalpel, with the narrow back-channel portion preferably close in proximity to the rearward end of the scalpel. The rearward guide also includes a wide fore-channel portion 49 that is located at the opposite end of the rearward guide from the narrow back-channel portion, toward the forward end 38 of the scalpel. The rearward wire guide expands from the narrow back-channel portion to the wide fore-channel portion, along the rearward guide length 44. A guide centerline 45 is formed through the pair of wire guides 28, as detailed in FIG. 4A. The guide centerline is the path that the wire 29 follows through the wire guides, and more specifically, the center of the path that the wire follows, when the wire is engaged by and seated within the pair of wire guides. The wire centerline 37, as detailed in FIG. 4B, approximately matches the guide centerline as detailed in FIG. 4A, when the wire runs through the pair of wire guides.

Figure 3B:
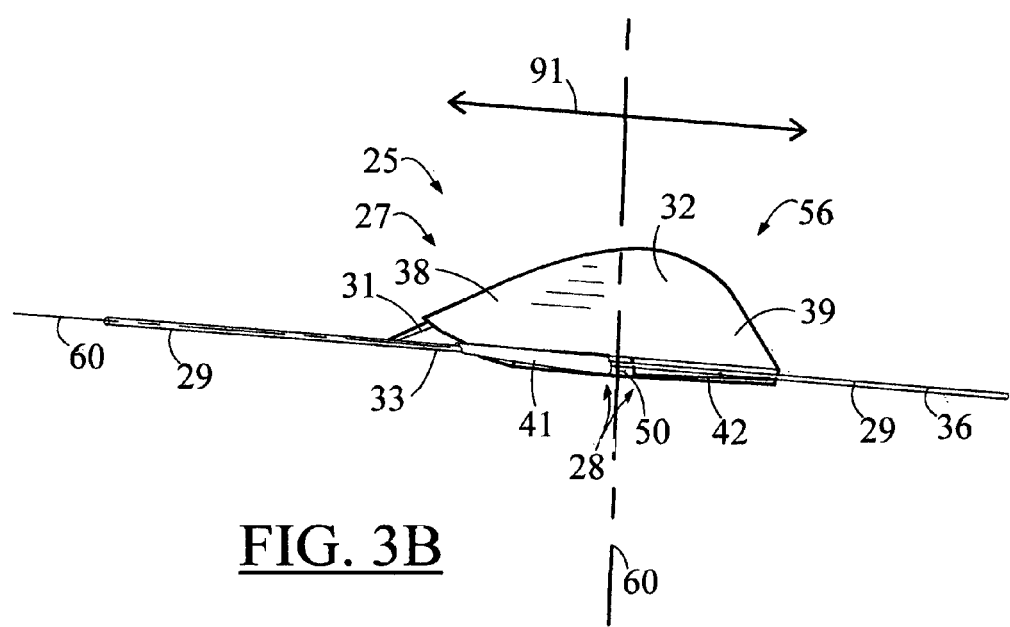
FIG. 3B is a perspective view of a guide system for a scalpel, according to an embodiment of the invention.

Additionally, as shown in FIGS. 3A, 3B, 4A, and 4B, a medial gap 50 is formed in the scalpel 27, between the forward guide 41 and the rearward guide 42. To attach the scalpel to the wire 29, the medial gap of the scalpel is orientated and placed at an oblique angle, upon the continuous length 36 of the wire. Specifically, the scalpel receives the continuous length of the wire by the user grasping the handle 32 to engage the wire into the pair of wire guides 28 with an oblique placement 55 of the scalpel's medial gap on the continuous length of the wire, as shown in FIG. 3A. This oblique placement is followed by an engagement rotation 90 of the scalpel on an "axis of rotation" 60. The axis of rotation 60 is a line that passes through the scalpel at the medial gap 50. As shown in FIGS. 3A and 3B, the axis of rotation is perpendicular to the wire centerline 37, and the final position of the scalpel engagement to the wire is accomplished when the guide centerline 45 of the scalpel, as again shown in FIG. 3A, approximately matches the wire centerline of the wire, as shown in FIG. 3B.

The terms "approximately" or "approximate" are employed herein throughout, including this detailed description and the attached claims, with the understanding that is denotes a level of exactness as typical for the skill and precision of the applicable field of medical endeavor.

Importantly, the attachment of the scalpel 27 to the pair of wire guides wire 28 is accomplished without threading an end of the wire 29 through the pair of wire guides. The oblique placement 55 and engagement rotation 90 of the scalpel onto the wire can be further described in a stepwise description. To initiate the attachment of the scalpel to the wire, as shown in FIG. 3A, the scalpel is placed obliquely on or immediately next to the wire, proximate to the medial gap 50. This oblique placement of the scalpel is approximately at a right angle to the wire, with the wire centerline 37 at the approximate ninety-degree angle in relation to the guide centerline 45. However, a somewhat more-or-less oblique angle may function, just as well, depending on factors such as the size and shape of the medial gap, along with the selected shapes of the wide back-channel portion 47 of the forward guide 41 and the wide fore-channel portion 49 of the rearward guide 42.

The engagement rotation 90 of the scalpel 27 to the substantially parallel placement 56 in relation to the continuous length of the wire 29 is shown in FIGS. 3B and 4B. This engagement of the wire within the pair of wire guides 28 results in the wire being seated within the pair of wire guides in the substantially parallel placement. Furthermore, by the attachment of the scalpel to the wire, the pair of wire guides engage the wire, preferably without bending the wire in that the wire runs through the pair of wire guides without bending or kinking the wire. The pair of wire guides position the scalpel on the wire, thereby allowing the scalpel to move along the wire in the guided movement 91, with the wire held within the wire guides, as the scalpel is able to move or travel along the wire. As shown in FIG. 4B, the blade 31 of the scalpel is positionable immediately adjacent to the wire, so that incisions made by the blade as the scalpel moves along the wire are in close proximity to the guide wire. Most preferably, after engagement of the wire guides to the wire, the user 26 of the scalpel can initiate and control movement of the scalpel along the wire with a minimum of effort, the scalpel guided by the wire. Alternatively, the user can either advance or retract both the engaged scalpel and the wire together, as a single unit.

For a preferred embodiment of the scalpel guide system 25, the scalpel 27 is most preferably disposable, and the pair of wire guides 28 formed from the same plastic material as the handle 32 of the scalpel. For this disposable embodiment, the pair of wire guides are most preferably an integral part of the mold of the handle and so does not require any additional forming steps in the manufacture of the handle.

With the scalpel or other equivalent bladed surgical instrument 27 attached to the wire 29 with the pair of wire guides 28, as discussed above, the scalpel is re-positionable in a guided movement 91 along the wire. As first discussed above, the scalpel guide system 25 of the present invention is of great benefit in the well known Seldinger technique, aiding in the percutaneous introduction of a wide variety of catheter devices.

A key step in most percutaneous catheterization placements requires that the puncture site be enlarged to allow the larger diameter catheter to advance along the wire 29, into the enlarged incision at the puncture site. More broadly, any procedure employing a variation of the Seldinger technique can benefit from the scalpel guide system 25 of the present invention, with the scalpel re-positionable in the guided movement 91 along the portion of the continuous length 36 of the wire, as shown in FIG. 3B.

By guiding the scalpel 27 down the wire 29 with the aid of the pair of wire guides 28, the blade 31 of the scalpel can incise a tissue layer, with the pair of wire guides orienting the scalpel blade against the wire in a manner that allows the scalpel blade to be guided by the wire as it is advanced to make a dermatotomy that is precisely oriented to the point where the guidewire enters the tissue of the subject patient. The standard "#11" blade, designed to make "stab incisions," has been employed historically because its pointed blade tip easily enlarges the puncture site. Other standard blade types, or other blade configurations, could be employed as alternatives to the #11 blade. The pointed tip or point 35 is preferred to rounded tips, but either could be utilized with the system of the present invention.

In compliance with the statutes, the invention has been described in language more or less specific as to structural features and process steps. While this invention is susceptible to embodiment in different forms, the specification illustrates preferred embodiments of the invention with the understanding that the present disclosure is to be considered an exemplification of the principles of the invention, and the disclosure is not intended to limit the invention to the particular embodiments described. Those with ordinary skill in the art will appreciate that other embodiments and variations of the invention are possible, which employ the same inventive concepts as described above. Therefore, the invention is not to be limited except by the following claims, as appropriately interpreted in accordance with the doctrine of equivalents.

The following is claimed:

1. A bladed surgical instrument guide for receiving a wire onto the bladed surgical instrument, and for guiding the travel of a bladed surgical instrument along the wire; the guide comprising:

a pair of wire guides, each extending from a bladed surgical instrument;

the bladed surgical instrument includes a forward end and a rearward end;

the pair of wire guides includes a forward guide located proximate to the forward end of the bladed surgical instrument, and a rearward guide located proximate to the rearward end of the bladed surgical instrument;

the forward guide with a forward guide length parallel to a guide centerline, the guide centerline defined as a path that a wire follows through the pair of wire guides, when the wire is engaged by and seated within the pair of wire guides, and the forward guide includes a narrow fore-channel portion located proximate to the forward end of the bladed surgical instrument, and the forward guide includes a wide back-channel portion located toward the rearward end of the bladed surgical instrument, and the forward wire guide expands from the narrow fore-channel portion to the wide back-channel portion, along the forward guide length;

the rearward guide with a rearward guide length parallel to the guide centerline, and the rearward guide includes a narrow back-channel portion located proximate to the rearward end of the bladed surgical instrument, and the rearward guide includes a wide fore-channel portion located toward the forward end of the bladed surgical instrument, and the rearward wire guide expands from the narrow back-channel portion to the wide fore-channel portion, along the rearward guide length;

a medial gap between the forward guide and the rearward guide;

the wire engaged by the pair of wire guides with an oblique placement of a continuous length of the wire into the medial gap, followed by a rotation of the bladed surgical instrument to a substantially parallel placement in relation to the continuous length of the wire, without threading an end of the wire through the pair of wire guides, and the wire seated within the pair of wire guides in the substantially parallel placement; and the bladed surgical instrument re-positionable in a guided movement along the continuous length of the wire.

2. The bladed surgical instrument guide of claim 1, wherein:

the guide centerline includes the center of the path that the wire follows and is approximately located along the wire, when the wire is held within the pair of wire guides.

3. The bladed surgical instrument guide system of claim 1, wherein;

the pair of wire guides includes a wire centerline, and the wire centerline approximately matches the guide centerline, when the wire runs through the pair of wire guides.

4. The bladed surgical instrument guide system of claim 1, wherein;

the bladed surgical instrument is removably attachable from to the length of the wire, without threading the end of the wire through the pair of wire guides.

5. The bladed surgical instrument guide system of claim 1, wherein;

the bladed surgical instrument is a scalpel with a blade, and the blade is positionable immediately adjacent to the wire, to make incisions immediately adjacent and in close proximity to the guide wire with the blade, as the scalpel moves along the wire.

6. A bladed surgical instrument guide system, the guide system comprising:

a pair of wire guides, each extending from a bladed surgical instrument;

the bladed surgical instrument includes a forward end and a rearward end;

the pair of wire guides includes a forward wire guide located proximate to the forward end of the bladed surgical instrument, and a rearward guide located proximate to the rearward end of the bladed surgical instrument;

the forward guide has a forward guide length parallel to a guide centerline, the guide centerline defined as a path that the wire follows through the pair of wire guides, when the wire is engaged by and seated within the pair of wire guides, and the forward guide includes a narrow fore-channel portion located proximate to the forward end of the bladed surgical instrument, and the forward guide includes a wide back-channel portion located toward the rearward end of the bladed surgical instrument, and the forward wire guide expands from the narrow fore-channel portion to the wide back-channel portion, along the forward guide length;

the rearward guide with a rearward guide length parallel to the guide centerline, and the rearward guide includes a narrow back-channel portion located proximate to the rearward end of the bladed surgical instrument, and the rearward guide includes a wide fore-channel portion located toward the forward end of the bladed surgical instrument, and the rearward wire guide expands from the narrow back-channel portion to the wide fore-channel portion, along the length of the rearward guide;

a medial gap between the forward guide and the rearward guide;

the wire engaged by the pair of wire guides with a placement of a continuous length of the wire into the medial gap, followed by a rotation of the bladed surgical instrument to a substantially parallel placement of the bladed surgical instrument in relation to the continuous length of the wire, without threading an end of the wire through the pair of wire guides, and the wire seated within the pair of wire guides in the substantially parallel placement of the bladed surgical instrument relative to the wire; and the bladed surgical instrument re-positionable in a guided movement along the continuous length of the wire.

7. The bladed surgical instrument guide system of claim 6, wherein;

the rearward guide and the forward guide of the pair of wire guides each has a generally open funnel-shape.

8. The bladed surgical instrument guide system of claim 6, wherein;

the bladed surgical instrument is placed on the continuous length of the wire in an oblique placement, relative to the wire.

9. The bladed surgical instrument guide system of claim 6, wherein;

the guide centerline includes the center of the path that the wire follows and is approximately located along the wire, when the wire is held within the pair of wire guides.

10. The bladed surgical instrument guide system of claim 6, wherein;

the pair of wire guides includes a wire centerline, and the wire centerline approximately matches the guide centerline, when the wire runs through the pair of wire guides.

11. The bladed surgical instrument guide system of claim 6, wherein;

the bladed surgical instrument is removably attachable from to the length of the wire, without threading the end of the wire through the pair of wire guides.

12. The bladed surgical instrument guide system of claim 6, wherein;

the bladed surgical instrument is a scalpel with a blade, and the blade is positionable immediately adjacent to the wire, to make incisions immediately adjacent and in close proximity to the guide wire with the blade, as the scalpel moves along the wire.

* * * * *